United States Patent [19]
Hattori et al.

[11] Patent Number: 5,624,812
[45] Date of Patent: Apr. 29, 1997

[54] METHOD FOR MEASURING CARBON DIOXIDE AND REAGENT THEREFOR

[75] Inventors: Shizuo Hattori; Takahide Kishimoto; Yukihiro Sogabe; Shigenori Emi, all of Tsuruga, Japan

[73] Assignee: Toyo Boseki Kabushiki Kaisha, Osaka, Japan

[21] Appl. No.: 467,768

[22] Filed: Jun. 6, 1995

Related U.S. Application Data

[63] Continuation-in-part of Ser. No. 210,559, Mar. 18, 1994, Pat. No. 5,547,851.

[30] Foreign Application Priority Data

Mar. 22, 1993 [JP] Japan ................................. 5-61987

[51] Int. Cl.$^6$ ................................. C12Q 1/25; G01N 33/50
[52] U.S. Cl. ................................. 435/26; 435/823; 422/84
[58] Field of Search ................................. 435/26, 823; 422/84

[56] References Cited

U.S. PATENT DOCUMENTS 3,963,578  6/1976  Aitken et al. ................................. 435/823

OTHER PUBLICATIONS

Tietz, et al, 1986, Clinical Chemistry, W.B. Saunders Co., London, pp. 1188–1189, 1190.

*Primary Examiner*—Helen Pratt
*Attorney, Agent, or Firm*—Leydig, Voit & Mayer, Ltd.

[57] ABSTRACT

A method for measuring carbon dioxide, comprising the steps of: (1) reacting bicarbonate ion in a sample with phosphoenolpyruvate carboxylase derived from an acetic acid bacterium in the presence of phosphoenolpyruvate; (2) reacting the resultant oxalacetic acid with malate dehydrogenase in the presence of NADH; and (3) measuring decreased NADH, and a reagent for measuring carbon dioxide, comprising phosphoenolpyruvate, phosphoenolpyruvate carboxylase derived from an acetic acid bacterium, malate dehydrogenase, NADH and a buffer. According to the present invention, a highly stable reagent for $CO_2$ measurement, which permits a long-term storage in a liquid state, can be provided by the use of phosphoenolpyruvate carboxylase derived from a species of acetic acid bacteria.

15 Claims, 9 Drawing Sheets

METHOD FOR MEASURING CARBON DIOXIDE AND REAGENT THEREFOR

The present application is a continuation-in-part of U.S. Ser. No. 08/210,559, filed Mar. 18, 1994 now U.S. Pat. No. 5,547,851.

FIELD OF THE INVENTION

The present invention relates to a method for measuring carbon dioxide in body fluids, particularly in blood serum or blood plasma, and to a reagent therefor.

BACKGROUND OF THE INVENTION

Carbon dioxide in blood serum or blood plasma is in an equilibrium with bicarbonate ion ($HCO_3^-$) and is a second largest fraction in blood serum and blood plasma. Therefore, the carbon dioxide forms the most important biological buffering action system in blood. The carbon dioxide content in blood serum or blood plasma is a significant index of electrolytic dispersion and shortage of anion, to aid medical diagnosis of acid-base inequilibrium in the respiratory system and metabolism. For example, normal bicarbonate ion concentration in blood serum and blood plasma is 22–32 mmol/l and a decrease to a low value of 15 mmol/l or an increase to a high value of 40 mmol/l suggests presence of abnormality.

While a carbon dioxide level in body fluids can be measured by various methods, it is generally measured by tracing the changes caused by the enzyme reaction to be mentioned later. When phosphoenolpyruvate carboxylase is reacted with bicarbonate ion and phosphoenolpyruvic acid, oxalacetic acid and phosphoric acid are produced. The resultant oxalacetic acid is reacted with malate dehydrogenase in the presence of NADH, and a decrease in NADH is measured by a known method such as an end point method or a rate method.

In the alkaline pH range, the equilibrium between carbon dioxide and bicarbonate ion shifts toward the reaction to form bicarbonate ion, and carbon dioxide exists as bicarbonate ion; in the acidic pH range, it forms $CO_2$ gas which is released into the air. For this reason, buffers having pH of 8.0 or above are generally used for a reagent for determining carbon dioxide.

The basic problem associated therewith is that phosphoenolpyruvate carboxylase is unstable in the alkaline pH range, with the result that a reagent for carbon dioxide measurement containing this enzyme cannot be stored for a long time in a liquid state. The phosphoenolpyruvate carboxylases available in the market are mostly derived from plants such as maize leaves and wheat germ, and show extremely poor stability at pH 8.0.

There is also known measurement of bicarbonate ion by the use of phosphoenolpyruvate carboxylase derived from Hyphomicrobium (EP 456444). This enzyme has a microbial origin, is free of the above-mentioned defects that the plant-originated phosphoenolpyruvate carboxylase has, and shows relatively high stability. It has been found, however, that this enzyme is not sufficiently stable at the enzyme concentration (generally 0.05–5 U/ml) that a reagent for measuring carbon dioxide generally has.

In the measurement method as disclosed in U.S. Pat. No. 3,974,037, phosphoenolpyruvate carboxylase derived from *Escherichia coli* is used. This enzyme shows poor stability in a reagent solution for measuring carbon dioxide which is weak alkaline.

Accordingly, a phosphoenolpyruvate carboxylase which is stable in a buffer (having a pH of about 8.0–8.5) to be contained in the $CO_2$ measurement reagent is demanded.

SUMMARY OF THE INVENTION

As a result of the intensive studies, the present inventors have now found that a phosphoenolpyruvate carboxylase produced by acetic acid bacteria is stable in a weak alkaline reagent solution for measuring carbon dioxide.

Accordingly, the present invention relates to a method for measuring carbon dioxide, comprising the steps of:

(1) reacting, in the presence of phosphoenolpyruvate, bicarbonate ion in a sample with phosphoenolpyruvate carboxylase derived from acetic acid bacteria;

(2) reacting the resultant oxalacetic acid with malate dehydrogenase in the presence of NADH; and (3) measuring the decreased NADH.

In addition, the present invention relates to a reagent for measuring carbon dioxide, comprising phosphoenolpyruvate, phosphoenolpyruvate carboxylase derived from acetic acid bacteria, malate dehydrogenase, NADH and a buffer.

The present inventors have found that, when using a phosphoenolpyruvate carboxylase derived from a species of acetic acid bacteria selected from the group consisting of *Acetobacter pasteurianus*, *Acetobacter xylinum* and *Gluconobacter oxydans*, the reactivity of phosphoenolpyruvate carboxylase becomes high in the presence of 50–100 mM magnesium ion and the reaction proceeds quickly.

DETAILED DESCRIPTION OF THE INVENTION

In the present invention, acetic acid bacteria mean the bacteria which oxidate ethyl alcohol to produce acetic acid.

The phosphoenolpyruvate carboxylase usable in the present invention can be obtained from almost all acetic acid bacteria, such as those belonging to the genus Acetobacter, the genus Gluconobacter, the genus Frateuria and the genus Acidomonas. It is preferable from the economical point of view that bacteria capable of yielding phosphoenolpyruvate carboxylase in a remarkably large amount be used from among these bacteria. Preferred are the enzymes derived from *Acetobacter pasteurianus*, *Acetobacter xylinum*, *Acetobacter hansenii* or *Gluconobacter oxydans*. Specific examples thereof include enzymes derived from *Acetobacter hansenii* IFO 14820 (ATCC 35959), *Acetobacter Pasteurianus* IFO 14814 (ATCC 23768), *Acetobacter xylinum* IFO 15237 (NCIB 11664) or *Gluconobacter oxydans* IFO 3462 (NRRL B-1225).

Of these, *Acetobacter hansenii* ATCC 35959 and *Acetobacter pasteurianus* ATCC 23768 are available from American Type Culture Collection, Rockville, Md., USA; *Acetobacter xylinum* NCIB 11664 is available from National Collection of Industrial and Marine Bacteria, Aberdeen, Scotland, United Kingdom; and *Gluconobacter oxydans* NRRL B-1225 is available from Agricultural Research Service Culture Collection, Peoria, Ill., USA.

The phosphoenolpyruvate carboxylase produced by acetic acid bacteria has been reported in known literatures as being obtainable from, for example, *Acetobacter aceti* [Arch. Microbiol., 122, 109 (1979)] or *Acetobacter xylinum* [J. Bacteriol., 98, 1005 (1969)]. The phosphoenolpyruvate carboxylase to be used in the present invention is also obtainable by purification according to the methods described in those literatures.

Purification of phosphoenolpyruvate carboxylase, which can be suitably used in the present invention and is derived from *Acetobacter hansenii*, is shown in the following.

For example, *Acetobacter hansenii* IFO 14820 (ATCC 35959) is cultured in a nutrient medium. After harvesting, the cells are suspended in 50 mM potassium phosphate buffer (pH 7.0) and crushed by a French press. After centrifugation, 30–50% ammonium sulfate fractions are obtained from the culture supernatant. The obtained enzyme solution is purified by ion-exchange chromatography, hydroxyapatite chromatography etc. to give an enzyme solution containing about 25 U/mg protein. This method is also applicable to the purification of phosphoenolpyruvate carboxylase yielded by different bacteria belonging to acetic acid bacteria.

The above-mentioned phosphoenolpyruvate carboxylase yielded by *Acetobacter hansenii* has the following physico-chemical properties.

Km value: 0.21 mM (for phosphoenolpyruvate)
Optimal pH: 7.5–8.0
Optimal temperature: 60° C.
Molecular weight: about 390,000 (gel filtration)
Not activated by acetyl CoA.
Not inhibited by ADP.

The activity of the phosphoenolpyruvate carboxylase can be determined according to the following method.

A reaction mixture (2.9 ml) containing 50 mM Tris-HCl, 10 mM $Na_2CO_3$, 3.2 mM phosphoenolpyruvic acid, 100 mM $MgSO_4$, 0.14 mM NADH and 50 U/ml malate dehydrogenase is prepared in a cuvette (d=1 cm) and preheated at 30° C. for about 5 minutes. An enzyme solution (0.1 ml) is added thereto and the mixture is gently stirred. A change in absorbance at 340 nm is recorded for 2–3 minutes with a spectrophotometer using water adjusted to 30° C. as a control, and change in absorbance per minute is calculated from the initial linear portion thereof (ΔOD test). A blank test is performed by using 50 mM phosphate buffer (pH 7.0) in place of the enzyme solution and following the steps to determine changes in absorbance per minute (ΔOD blank). The activity of phosphoenolpyruvate carboxylase is calculated taking the enzyme amount consuming 1 micromole NADH in a minute under the above conditions as 1 unit (U).

Examples of the phosphoenolpyruvate to be used in the present invention include potassium salt, sodium salt, tricyclohexylammonium salt and monocyclohexylammonium salt.

Examples of the malate dehydrogenase usable in the present invention include those derived from swine heart, the genus Thermus and the genus Bacillus.

The buffer to be used in the present invention may be any insofar as it is weak alkaline (pH 8.0–8.5). Examples include Tris-HCl buffer, Tricine-HCl buffer and Good's buffer.

The method for measuring carbon dioxide follows the reactions shown by the formulas below.

oxalacetic acid + phosphoric acid wherein PEP is phosphoenolpyruvate, PEPC is phosphoenolpyruvate carboxylase and MDH is malate dehydrogenase.

Besides the phosphoenolpyruvate carboxylase derived from acetic acid bacteria, the reagent for $CO_2$ measurement of the present invention should contain phosphoenolpyruvate. The bicarbonate ion in the reagent generally produces oxalacetic acid from phosphoenolpyruvic acid by the action of the aforesaid phosphoenolpyruvate carboxylase under weak alkaline conditions. The oxalacetic acid is quantitatively determined using malate dehydrogenase in the presence of NADH, from the decrease of NADH which is caused by the production of malic acid from the oxalacetic acid. An end point method or a rate method is usable for this end.

The measurement of carbon dioxide is performed under weak alkaline conditions generally at pH 7.5–9.0, preferably pH 8.0–8.5.

The reagent of the present invention preferably contains 3–100 mM bivalent cation, such as magnesium ion ($Mg^{2+}$) and manganese ion ($Mn^{2+}$), as a cofactor, with preference given to magnesium ion. Examples of the substances which produce such bivalent cations include salts such as magnesium sulfate, magnesium chloride, manganese sulfate and manganese chloride.

When using a phosphoenolpyruvate carboxylase derived from a species of acetic acid bacteria selected from the group consisting of *Acetobacter pasteurianus*, *Acetobacter xylinum* and *Gluconobacter oxydans*, the reaction is carried out in a solution containing 50–100 mM magnesium ion. When the magnesium ion concentration is lower than 50 mM, the reactivity of phosphoenolpyruvate carboxylase becomes low, failing to end the reaction in a short time. On the other hand, too high a magnesium ion concentration may result in turbidity produced in the reaction mixture, which can prevent the assay. Accordingly, the magnesium ion concentration is preferably not more than 100 mM. When the magnesium ion concentration is 50–100 mM, the reactivity of phosphoenolpyruvate carboxylase derived from *Acetobacter pasteurianus*, *Acetobacter xylinum* or *Gluconobacter oxydans* becomes high, so that the reaction ends quickly generally within 5 minutes.

The reagent of the present invention generally has the following formulation.

| Weak alkaline buffer | 10–50 mM |
|---|---|
| Phosphoenolpyruvate | 2–5 mM |
| Magnesium ion | 3–100 mM |
| NADH | 0.3–1.5 mM |
| Malate dehydrogenase | 5–50 U/ml |
| Phosphoenolpyruvate carboxylase derived from acetic acid bacteria | 0.5–10 U/ml |

More specifically, the following formulation is exemplified.

| Tris-HCl buffer (pH 8.0) | 10–50 mM |
|---|---|
| Magnesium sulfate | 3–100 mM |
| Potassium phosphoenolpyruvate | 2–5 mM |
| NADH | 0.3–1.5 mM |
| Malate dehydrogenase | 5–50 U/ml |
| Phosphoenolpyruvate carboxylase derived from acetic acid bacteria | 0.5–5 U/ml |

So as to inhibit an interfering reaction by lactate dehydrogenase and pyruvic acid in a sample, addition of a lactate dehydrogenase inhibitor such as oxamate (e.g. sodium oxamate) at about 1–20 mM is desirable.

The above-mentioned reagent (1.5–3.0 ml) and a sample (0.01–0.1 ml) containing bicarbonate ion are mixed and allowed to react at 37° C. for 5–10 minutes, and decrease in absorbance at, for example, 340 nm, 365 nm or 380 nm is measured according to NADH concentration.

The above-mentioned formulation is for the end point method and for the rate method, the following formulation is generally suitable.

| Weak alkaline buffer | 10–50 mM |
|---|---|
| Phosphoenolpyruvate | 2–5 mM |
| Magnesium ion | 3–100 mM |
| NADH | 0.1–0.2 mM |
| Malate dehydrogenase | 5–50 U/ml |
| Phosphoenolpyruvate carboxylase derived from acetic acid bacteria | 0.05–1 U/ml |

More specifically, the following formulation is exemplified.

| Tris-HCl buffer (pH 8.0) | 10–50 mM |
|---|---|
| Magnesium sulfate | 3–100 mM |
| Potassium phosphoenolpyruvate | 2–5 mM |
| NADH | 0.1–0.2 mM |
| Malate dehydrogenase | 5–50 U/ml |
| Phosphoenolpyruvate carboxylase derived from acetic acid bacteria | 0.05–0.5 U/ml |

It is also preferable to add a lactate dehydrogenase inhibitor such as oxamate (e.g. sodium oxamate) at about 1–20 mM for the same reason as mentioned above with regard to the end point method.

When using a phosphoenolpyruvate carboxylase derived from a species of acetic acid bacteria selected from the group consisting of *Acetobacter pasteurianus*, *Acetobacter xylinum* and *Gluconobacter oxydans*, the reagent of the present invention to be used for the end method generally has the following formulation.

| Weak alkaline buffer | 10–50 mM |
|---|---|
| Phosphoenolpyruvate | 2–5 mM |
| Magnesium ion | 50–100 mM |
| NADH | 0.3–1.5 mM |
| Malate dehydrogenase | 5–50 U/ml |
| Phosphoenolpyruvate carboxylase | 0.5–10 U/ml |

A reagent having the following formulation is specifically exemplified.

| Tris-HCl buffer (pH 8.0) | 10–50 mM |
|---|---|
| Magnesium sulfate | 50–100 mM |
| Potassium phosphoenolpyruvate | 2–5 mM |
| NADH | 0.3–1.5 mM |
| Malate dehydrogenase | 5–50 U/ml |
| Phosphoenolpyruvate carboxylase | 0.5–10 U/ml |

When using a phosphoenolpyruvate carboxylase derived from a species of acetic acid bacteria selected from the group consisting of *Acetobacter pasteurianus*, *Acetobacter xylinum* and *Gluconobacter oxydans*, the reagent of the present invention to be used for the rate method generally has the following formulation.

| Weak alkaline buffer | 10–50 mM |
|---|---|
| Phosphoenolpyruvate | 2–5 mM |
| Magnesium ion | 50–100 mM |
| NADH | 0.1–0.2 mM |
| Malate dehydrogenase | 5–50 U/ml |
| Phosphoenolpyruvate carboxylase | 0.05–1 U/ml |

A reagent having the following formulation is specifically exemplified.

| Tris-HCl buffer (pH 8.0) | 10–50 mM |
|---|---|
| Magnesium sulfate | 50–100 mM |
| Potassium phosphoenolpyruvate | 2–5 mM |
| NADH | 0.1–0.2 mM |
| Malate dehydrogenase | 5–50 U/ml |
| Phosphoenolpyruvate carboxylase | 0.05–0.5 U/ml |

It is preferable that the reagent for the end method or the rate method contain a lactate dehydrogenase inhibitor. Specific examples and the amounts to be added of the lactate dehydrogenase inhibitor are as mentioned above.

The phosphoenolpyruvate carboxylase derived from acetic acid bacteria to be used in the present invention is superior in stability in the weak alkaline range as compared with phosphoenolpyruvate carboxylase of a different origin which is used in conventional methods.

Acetic acid bacteria grow well in the pH range from neutral to acidic and grow even at pH 2.0–3.0. The enzymes yielded thereby is also stable in the similar pH range and considered to be unstable in the weak alkaline range. Hence, it is beyond expectation that the phosphoenolpyruvate carboxylase derived from acetic acid bacteria is stable in a weak alkaline reagent for measuring carbon dioxide.

According to the present invention, a highly stable reagent for $CO_2$ measurement, which permits a long-term storage in a liquid state, can be provided by the use of phosphoenolpyruvate carboxylase derived from acetic acid bacteria.

When an enzyme of a different, conventionally-used origin is employed, the enzyme activity is degraded by 5% at a concentration used for a reagent for measuring carbon dioxide (about 3 U/ml), even after the storage at 9° C. for 7 days. The enzyme is completely deactivated after the storage at 25° C. for 7 days, as can be seen from the Comparative Examples to be described later. In contrast, the enzyme of the present invention retains nearly 100% activity after the storage at 9° C. for 7 days and shows residual activity even after the storage at 25° C. for 7 days.

The present invention is described in detail by illustrative Examples, to which the invention is not limited.

REFERENCE EXAMPLE 1

*Acetobacter hansenii* IFO 14820 (ATCC 35959) was cultured in a nutrient medium containing polypeptone (0.5%), yeast extract (0.5%), glucose (0.5%) and magnesium sulfate (0.05%) at 30° C. for 2 days with aeration, and the cells were crushed with a French press. After sulfate fractionation, the cells were purified by DEAE-Sepharose chromatography and hydroxyapatite chromatography to give phosphoenolpyruvate carboxylase standard enzyme product (specific activity 25 U/mg).

EXAMPLE 1

Using the phosphoenolpyruvate carboxylase standard enzyme product derived from *Acetobacter hansenii* IFO 14820 (ATCC 35959), as purified in Reference Example 1, the following reagent for measuring carbon dioxide was prepared.

| | |
|---|---|
| Tris-HCl buffer (pH 8.0) | 50 mM |
| Magnesium sulfate | 10 mM |
| Potassium phosphoenolpyruvate | 3.2 mM |
| NADH | 0.14 mM |
| Malate dehydrogenase | 50 U/ml |
| Phosphoenolpyruvate carboxylase | 0.3 U/ml |

Figure 1:
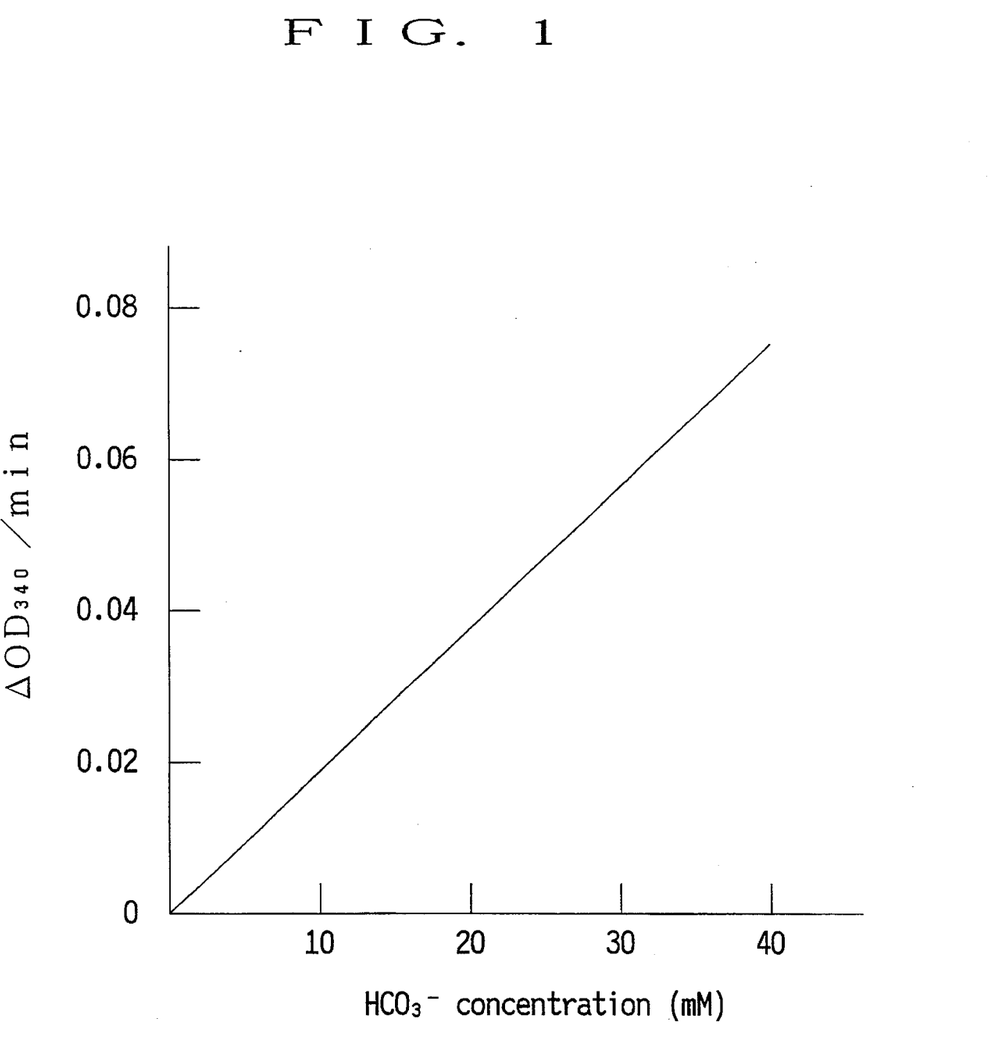
FIG. 1 shows the relationship between the concentration of bicarbonate ion in a sample and a decrease in the absorbance of NADH per minute, which is caused by the use of the reagent of the present invention.

The above-mentioned reagent (3.0 ml) and a sample (0.01 ml) containing bicarbonate ion (0–40 mM) were mixed and allowed to react at 37° C. for 3 minutes. Decrease in absorbance at 340 nm was measured (the value at bicarbonate ion concentration of 0 mM was subtracted as a blank value) (rate method). The relationship between the concentration of bicarbonate ion in the sample and decrease in the absorbance per minute is shown in FIG. 1. A linear relation existed between the concentration of bicarbonate ion and the change in absorbance.

EXAMPLE 2

Using the phosphoenolpyruvate carboxylase standard enzyme product derived from *Acetobacter hansenii* IFO 14820 (ATCC 35959), as purified in Reference Example 1, the following reagent for measuring carbon dioxide was prepared.

| | |
|---|---|
| Tris-HCl buffer (pH 8.0) | 50 mM |
| Magnesium sulfate | 10 mM |
| Potassium phosphoenolpyruvate | 3.2 mM |
| NADH | 0.5 mM |
| Malate dehydrogenase | 50 U/ml |
| Phosphoenolpyruvate carboxylase | 3 U/ml |

Figure 2:
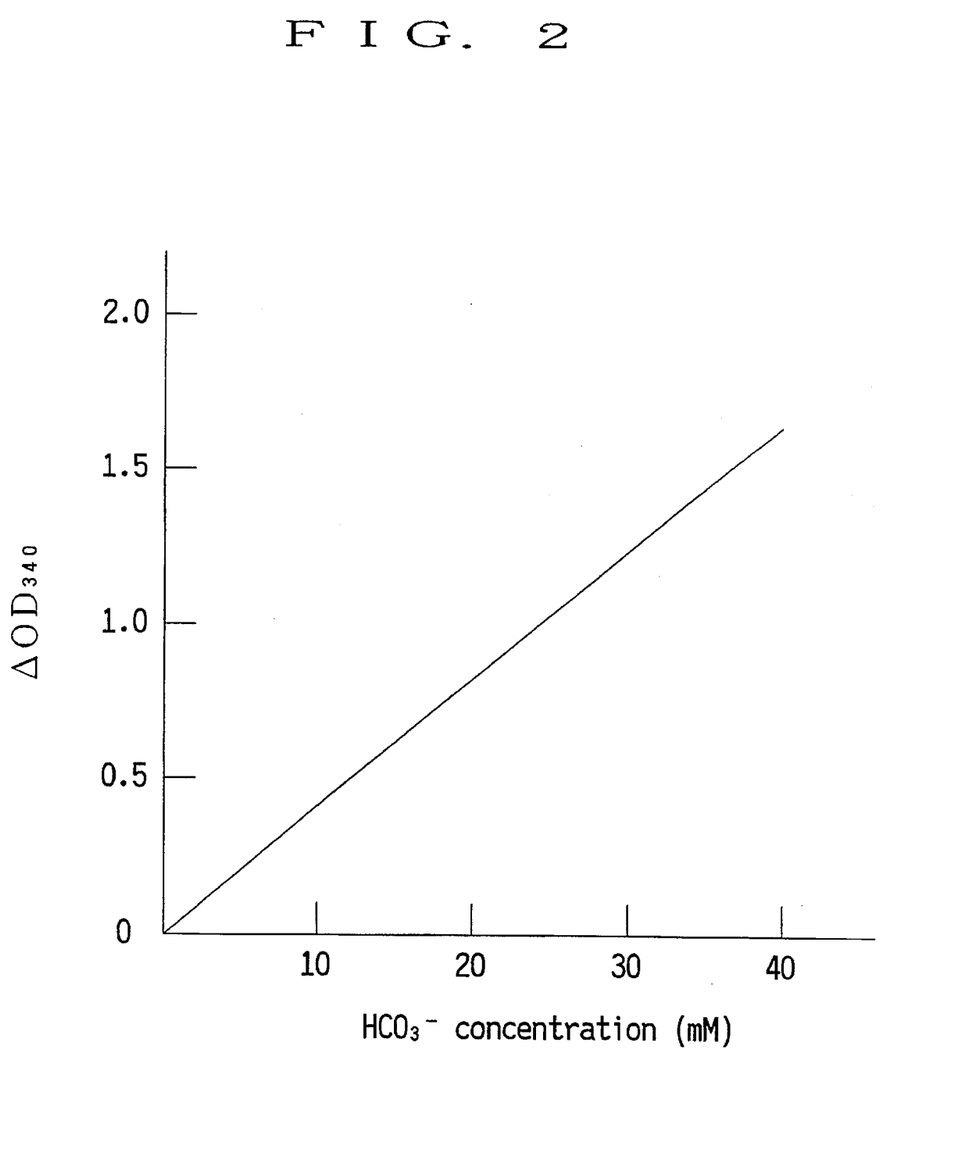
FIG. 2 shows the relationship between the concentration of bicarbonate ion in a sample and a decrease in the absorbance of NADH in 5 minutes, which is caused by the use of the reagent of the present invention.

The above-mentioned reagent (3.0 ml) and a sample (0.01 ml) containing bicarbonate ion (0–40 mM) were mixed and allowed to react at 37° C. for 5 minutes. Decrease in absorbance at 340 nm in 5 minutes was measured (the value at bicarbonate ion concentration of 0 mM was subtracted as a blank value) (end point method). The relationship between the concentration of bicarbonate ion in the sample and decrease in the absorbance in 5 minutes is shown in FIG. 2. A linear relation existed between the concentration of bicarbonate ion and the change in absorbance.

EXAMPLE 3

Figure 3:
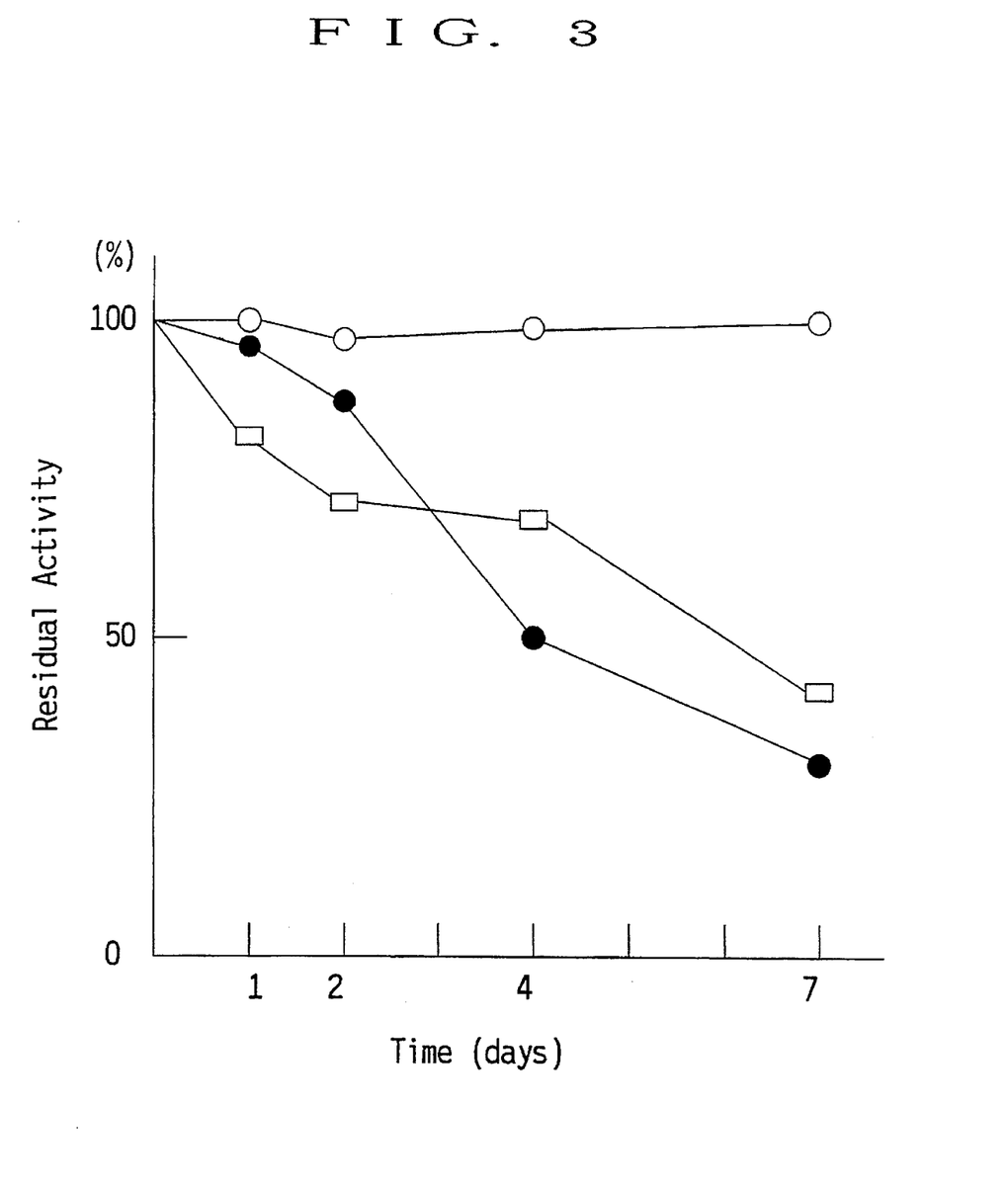
FIG. 3 shows the preservation stability of the reagent of the present invention, wherein ○ is at 9° C., ● is at 25° C. and □ is at 40° C.

The reagent for measuring carbon dioxide as obtained in Example 2 was preserved at 9° C., 25° C. or 40° C. and the activity of phosphoenolpyruvate carboxylase in the reagent was measured at day 0, day 1, day 2, day 4 and day 7. The results are shown in FIG. 3. After preservation for 7 days, the residual activity was 100% (9° C.), 31% (25° C.) and 41% (40° C.).

COMPARATIVE EXAMPLE 1

Figure 4:
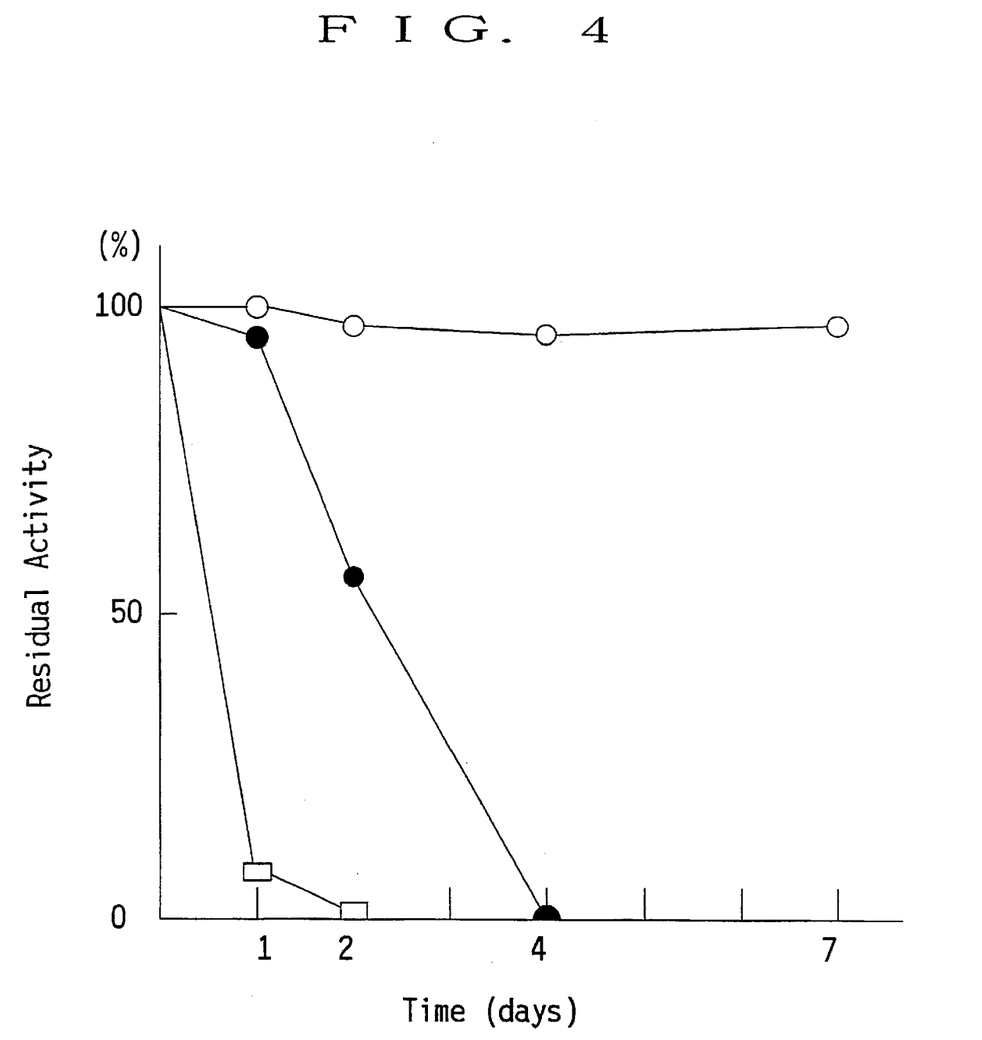
FIG. 4 shows the preservation stability of a reagent for comparison, wherein ○ is at 9° C., ● is at 25° C. and □ is at 40° C.

Using phosphoenolpyruvate carboxylase derived from maize leaves (Biozyme), a reagent for measuring carbon dioxide which had the same formulation as the reagent of Example 2 was prepared. The reagent was preserved at 9° C., 25° C. or 40° C. and the enzyme activity was measured at day 0, day 1, day 2, day 4 and day 7. The results are shown in FIG. 4. After preservation for 7 days, the residual activity was 20% (9° C.), 0% (25° C.) and 0% (40° C.). The enzyme derived from corn showed inferior stability as compared with the enzyme derived from acetic acid bacteria.

REFERENCE EXAMPLE 2

*Hyphomicrobium methylovorum* IFO 14180 was cultured in a nutrient medium containing methanol (1.0%), diammonium phosphate (0.3%), dipotassium phosphate (0.2%), sodium chloride (0.2%), magnesium sulfate (0.02%) and various vitamins at 30° C. for 4 days and the cells were crushed with a French press. After sulfate fractionation, the cells were purified by DEAE-Sepharose chromatography and hydroxyapatite chromatography to give a phosphoenolpyruvate carboxylase standard enzyme product (specific activity 20 U/mg).

COMPARATIVE EXAMPLE 2

Using the phosphoenolpyruvate carboxylase obtained in Reference Example 2, a reagent for measuring carbon dioxide which had the same formulation as the reagent of Example 2 was prepared. The reagent was preserved at 9° C., 25° C. or 40° C. and the enzyme activity was measured at day 0, day 1, day 4 and day 7.

Figure 5:
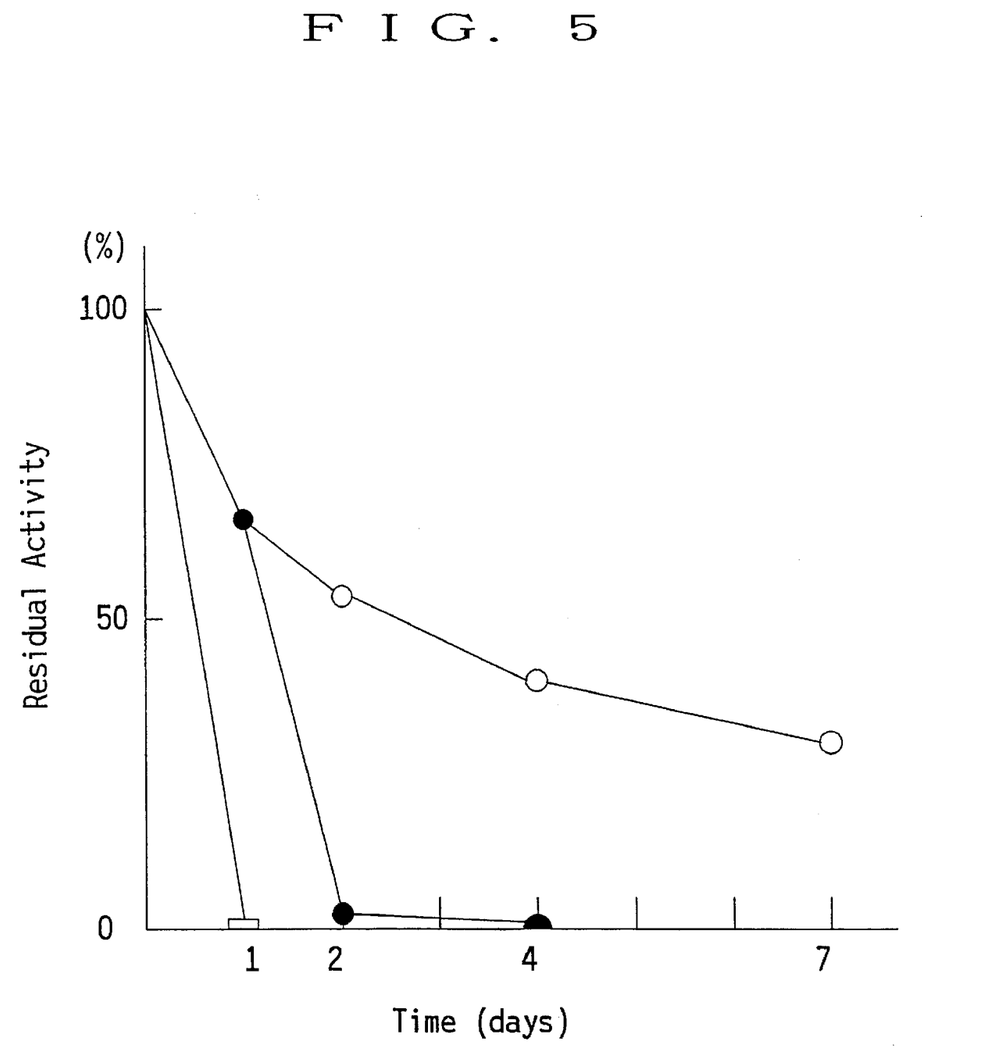
FIG. 5 shows the preservation stability of a reagent for comparison, wherein ○ is at 9° C., ● is at 25° C. and □ is at 40° C.

The results are shown in FIG. 5. After preservation for 7 days, the residual activity was 95% (9° C.), 0% (25° C.) and 0% (40° C.). The enzyme derived from Hyphomicrobium showed inferior stability as compared with the enzyme derived from acetic acid bacteria.

COMPARATIVE EXAMPLE 3

According to the method described in U.S. Pat. No. 3,974,037, phosphoenolpyruvate carboxylase derived from *Escherichia coli* was purified. Using said enzyme, a reagent for measuring carbon dioxide which had the same formulation as the reagent of Example 2 was prepared. Acetyl CoA was added to the reagent (1 mM). The reagent was preserved at 25° C. and the enzyme activity was measured at day 0 and day 4. The residual activity at day 4 was 4%. The enzyme derived from *Escherichia coli* showed inferior stability as compared with the enzyme derived from acetic acid bacteria.

EXAMPLE 4

*Acetobacter pasteurianus* IFO 14814 (ATCC 23768) was cultured in a nutrient medium and purified by a known method to give a phosphoenolpyruvate carboxylase standard enzyme product (specific activity 25 U/mg). Using said standard product, a reagent for measuring carbon dioxide which had the same formulation as the reagent of Example 2 was prepared. The concentration of magnesium sulfate was 100 mM. In the same manner, enzyme products were prepared from *Acetobacter xylinum* IFO 15237 (NCIB 11664) and *Gluconobacter oxydans* IFO 3462 (NRRL B-1225) and prepared into reagents for $CO_2$ measurement.

The reagents were preserved at 9° C., 25° C. or 40° C. and the enzyme activity was measured at day 0, day 1, day 2, day 4 and day 7. The results are shown in Table 1. All reagents showed higher stability as compared with the reagents obtained from conventional enzymes.

TABLE 1

| Storage time | Residual activity in reagents for measuring carbon dioxide | | | | | | | | |
|---|---|---|---|---|---|---|---|---|---|
| | *A. pasteurianus* | | | *A. xylinum* | | | *G. oxydans* | | |
| | 9° C. | 25° C. | 40° C. | 9° C. | 25° C. | 40° C. | 9° C. | 25° C. | 40° C. |
| Day 0 | 100% | 100% | 100% | 100% | 100% | 100% | 100% | 100% | 100% |
| Day 1 | 102% | 99% | 86% | 102% | 100% | 92% | 100% | 98% | 15% |
| Day 2 | 100% | 83% | 80% | 100% | 78% | 80% | 101% | 55% | 5% |
| Day 4 | 100% | 62% | 75% | 100% | 44% | 60% | 99% | 30% | 0% |
| Day 7 | 99% | 54% | 66% | 101% | 21% | 35% | 99% | 10% | 0% |

The stability of phosphoenolpyruvate carboxylase derived from acetic acid bacteria or a different origin, in a reagent for measuring carbon dioxide (pH 8.0), was compared based on the residual activity after preservation at 25° C. for 4 days. The results are shown in Table 2.

TABLE 2

Stability in reagent for measuring carbon dioxide (25° C., 4 days)

| Origin | Residual activity |
|---|---|
| *Acetobacter hansenii* | 50% |
| *Acetobacter pasteurianus* | 62% |
| *Acetobacter xylinum* | 44% |
| *Gluconobacter oxydans* | 30% |
| Maize leaves | 0% |
| *Hyphomicrobium methylovorum* | 0% |
| *Escherichia coli* | 4% |

It is evident that the reagent of the present invention is superior in stability as compared with conventional reagents for measuring carbon dioxide.

EXAMPLE 5

Using the phosphoenolpyruvate carboxylase standard enzyme product derived from *Acetobacter xylinum* IFO 15237 (NCIB 11664), as purified according to the description in J. bacteriol., 98, 1005 (1969), the following reagent for measuring carbon dioxide was prepared.

| | |
|---|---|
| Tris-HCl buffer (pH 8.0) | 50 mM |
| Potassium phosphoenolpyruvate | 3.2 mM |
| Magnesium sulfate | 50 mM |
| NADH | 1.4 mM |
| Malate dehydrogenase | 8 U/ml |
| Phosphoenolpyruvate carboxylase | 10 U/ml |

Figure 6:
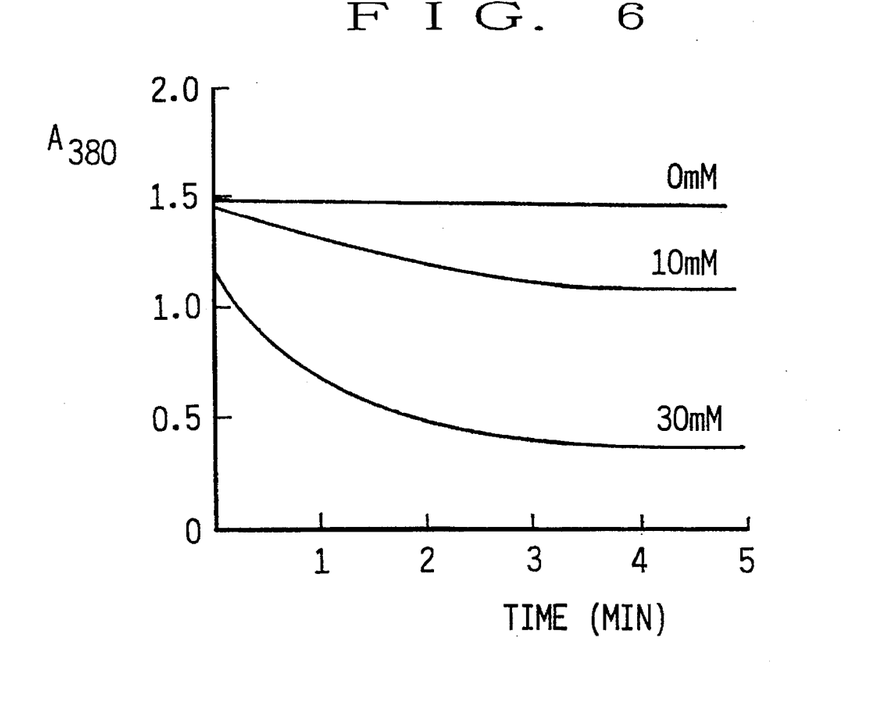
FIG. 6 shows changes in absorbance when the reagent of Example 5 was used.

The above-mentioned reagent (3.0 ml) and a sample (0.1 ml) containing bicarbonate ion (0, 10 or 30 mM) were mixed and allowed to react at 30° C. for 5 minutes. Decrease in absorbance at 380 nm was measured. The results are shown in FIG. 6. When the concentration of magnesium sulfate was 50 mM, the reaction proceeded quickly and ended in 4 minutes.

EXAMPLE 6

Using the phosphoenolpyruvate carboxylase standard enzyme product derived from *Acetobacter xylinum* IFO 15237 (NCIB 11664), which was obtained in Example 5, the following reagent for measuring carbon dioxide was prepared.

| | |
|---|---|
| Tris-HCl buffer (pH 8.0) | 50 mM |
| Potassium phosphoenolpyruvate | 3.2 mM |
| Magnesium sulfate | 100 mM |
| NADH | 1.4 mM |
| Malate dehydrogenase | 8 U/ml |
| Phosphoenolpyruvate carboxylase | 10 U/ml |

Figure 7:
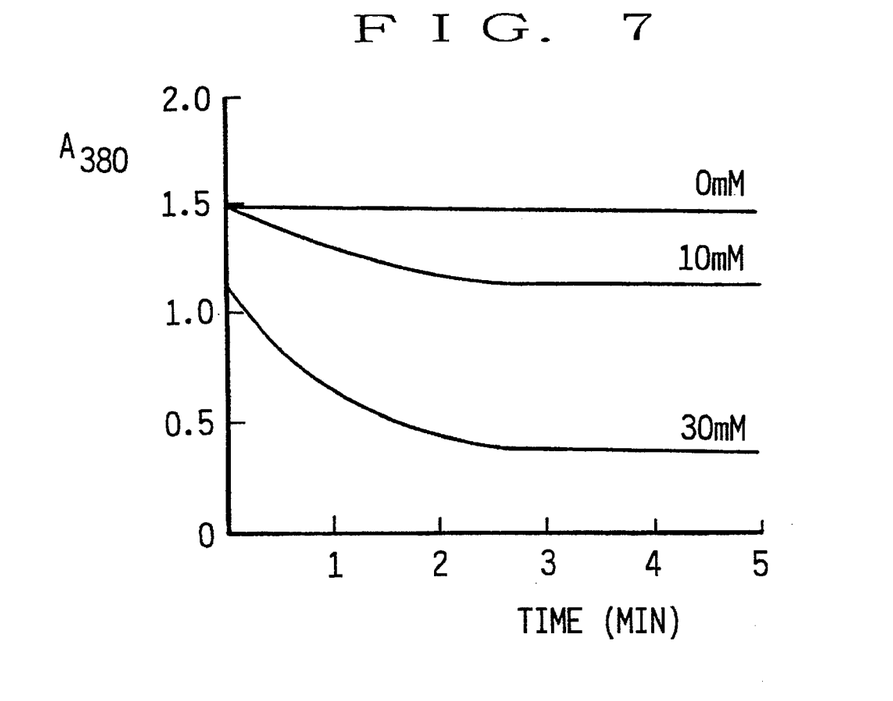
FIG. 7 shows changes in absorbance when the reagent of Example 6 was used.

The above-mentioned reagent (3.0 ml) and a sample (0.1 ml) containing bicarbonate ion (0, 10 or 30 mM) were mixed and allowed to react at 30° C. for 5 minutes. Decrease in absorbance at 380 nm was measured. The results are shown in FIG. 7. When the concentration of magnesium sulfate was 100 mM, the reaction proceeded quickly and ended in 3 minutes.

COMPARATIVE EXAMPLE 4

Using the phosphoenolpyruvate carboxylase standard enzyme product derived from *Acetobacter xylinum* IFO 15237 (NCIB 11664) obtained in Example 5, the following reagent for measuring carbon dioxide was prepared.

| | |
|---|---|
| Tris-HCl buffer (pH 8.0) | 50 mM |
| Potassium phosphoenolpyruvate | 3.2 mM |
| Magnesium sulfate | 10 mM |
| NADH | 1.4 mM |
| Malate dehydrogenase | 8 U/ml |
| Phosphoenolpyruvate carboxylase | 10 U/ml |

Figure 8:
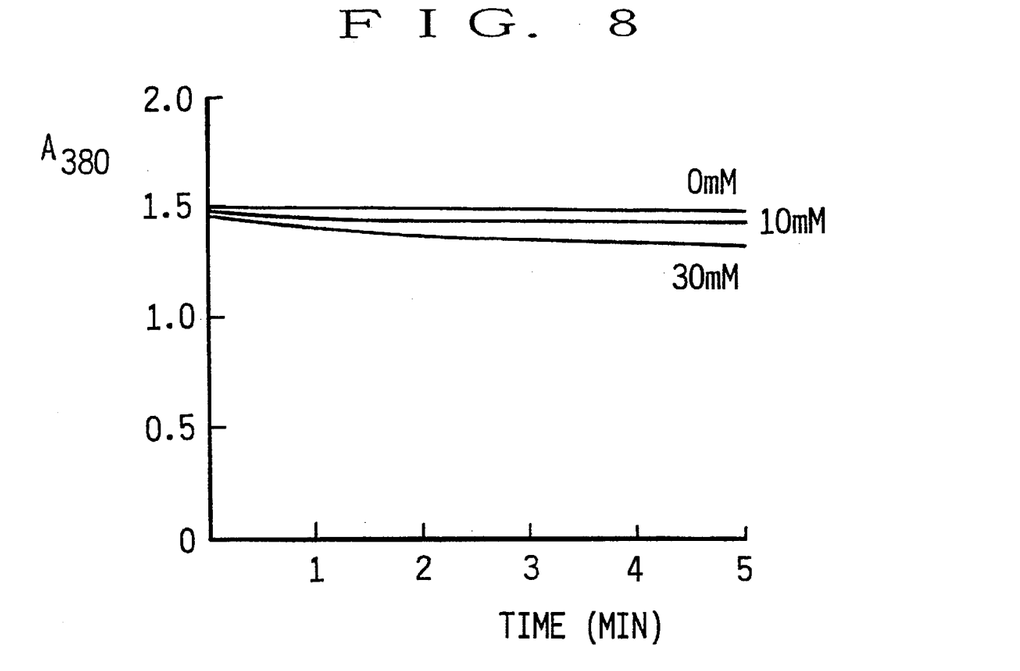
FIG. 8 shows changes in absorbance when the reagent of Comparative Example 4 was used.

The above-mentioned reagent (3.0 ml) and a sample (0.1 ml) containing bicarbonate ion (0, 10 or 30 mM) were mixed and allowed to react at 30° C. for 5 minutes. Decrease in absorbance at 380 nm was measured. The results are shown in FIG. 8. The reaction did not end even after 5 minutes, and the reactivity of the phosphoenolpyruvate carboxylase was markedly inferior.

EXAMPLE 7

Using a phosphoenolpyruvate carboxylase standard enzyme product derived from *Acetobacter pasteurianus* IFO 14814 (ATCC 23768), the following reagent for measuring carbon dioxide was prepared.

| Tris-HCl buffer (pH 8.0) | 50 mM |
| --- | --- |
| Potassium phosphoenolpyruvate | 3.2 mM |
| Magnesium sulfate | 50 mM |
| NADH | 1.4 mM |
| Malate dehydrogenase | 8 U/ml |
| Phosphoenolpyruvate carboxylase | 10 U/ml |

Figure 9:
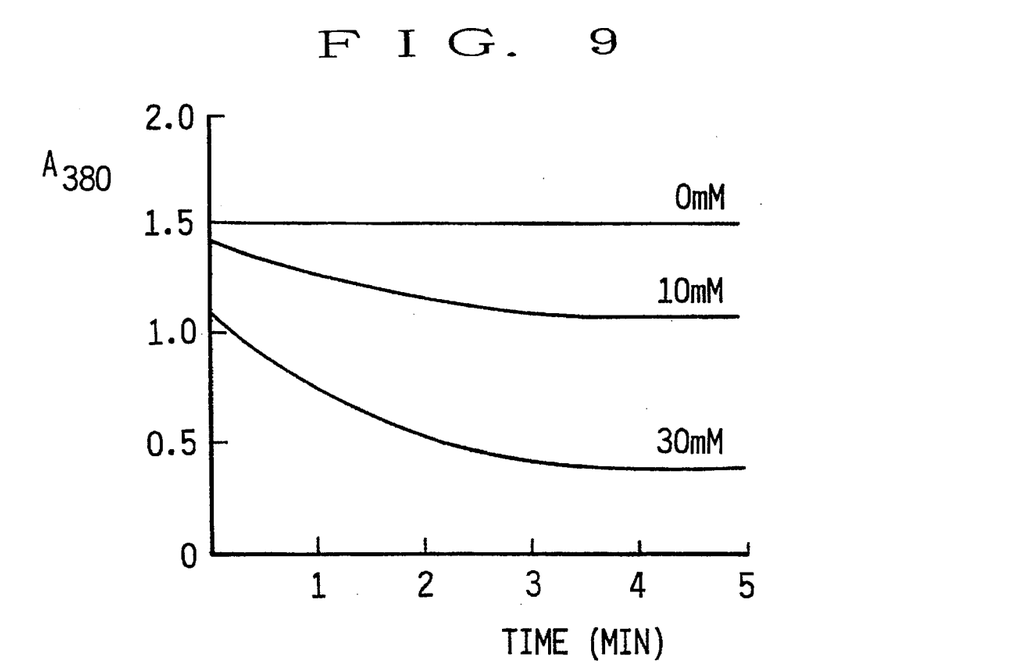
FIG. 9 shows changes inabsorbance when the reagent of Example 7 was used.

The above-mentioned reagent (3.0 ml) and a sample (0.1 ml) containing bicarbonate ion (0, 10 or 30 mM) were mixed and allowed to react at 30° C. for 5 minutes. Decrease in absorbance at 380 nm was measured. The results are shown in FIG. 9. When the concentration of magnesium sulfate was 50 mM, the reaction proceeded quickly and ended in 4 minutes.

EXAMPLE 8

Using the phosphoenolpyruvate carboxylase standard enzyme product derived from *Acetobacter pasteurianus* IFO 14814 (ATCC 23768, the following reagent for measuring carbon dioxide was prepared.

| Tris-HCl buffer (pH 8.0) | 50 mM |
| --- | --- |
| Potassium phosphoenolpyruvate | 3.2 mM |
| Magnesium sulfate | 100 mM |
| NADH | 1.4 mM |
| Malate dehydrogenase | 8 U/ml |
| Phosphoenolpyruvate carboxylase | 10 U/ml |

Figure 10:
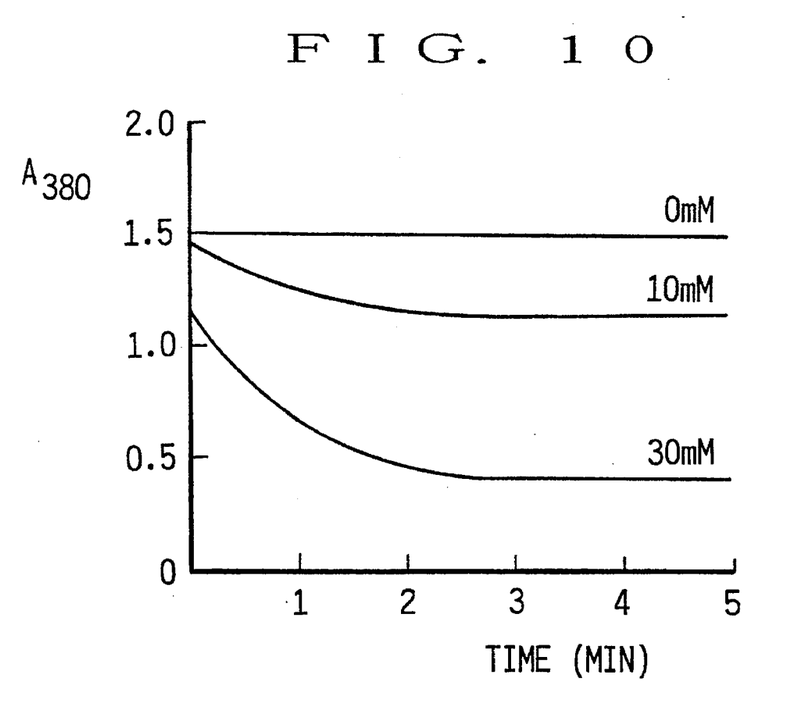
FIG. 10 shows changes in absorbance when the reagent of Example 8 was used.

The above-mentioned reagent (3.0 ml) and a sample (0.1 ml) containing bicarbonate ion (0, 10 or 30 mM) were mixed and allowed to react at 30° C. for 5 minutes. Derease in absorbance at 380 nm was measured. The results are shown in FIG. 10. When the concentration of magnesium sulfate was 100 mM, the reaction proceeded quickly and ended in 3 minutes.

EXAMPLE 9

Using a phosphoenolpyruvate carboxylase standard enzyme product derived from *Gluconobacter oxydans* IFO 3462 (NRRL B-1225), the following reagent for measuring carbon dioxide was prepared.

| Tris-HCl buffer (pH 8.0) | 50 mM |
| --- | --- |
| Potassium phosphoenolpyruvate | 3.2 mM |
| Magnesium sulfate | 50 mM |
| NADH | 1.4 mM |
| Malate dehydrogenase | 8 U/ml |
| Phosphoenolpyruvate carboxylase | 10 U/ml |

Figure 11:
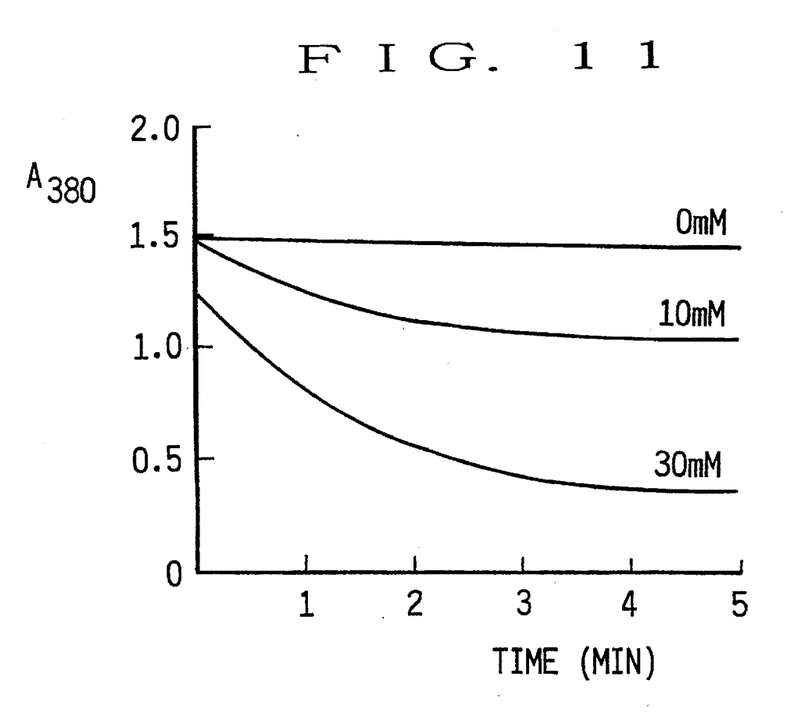
FIG. 11 shows changes in absorbance when the reagent of Example 9 was used.

The above-mentioned reagent (3.0 ml) and a sample (0.1 ml) containing bicarbonate ion (0, 10 or 30 mM) were mixed and allowed to react at 30° C. for 5 minutes. Decrease in absorbance at 380 nm was measured. The results are shown in FIG. 11. When the concentration of magnesium sulfate was 50 mM, the reaction proceeded quickly and ended in 4 minutes.

EXAMPLE 10

Using a phosphoenolpyruvate carboxylase standard enzyme product derived from *Gluconobacter oxydans* IFO 3462 (NRRL B-1225), the following reagent for measuring carbon dioxide was prepared.

| Tris-HCl buffer (pH 8.0) | 50 mM |
| --- | --- |
| Potassium phosphoenolpyruvate | 3.2 mM |
| Magnesium sulfate | 100 mM |
| NADH | 1.4 mM |
| Malate dehydrogenase | 8 U/ml |
| Phosphoenolpyruvate carboxylase | 10 U/ml |

Figure 12:
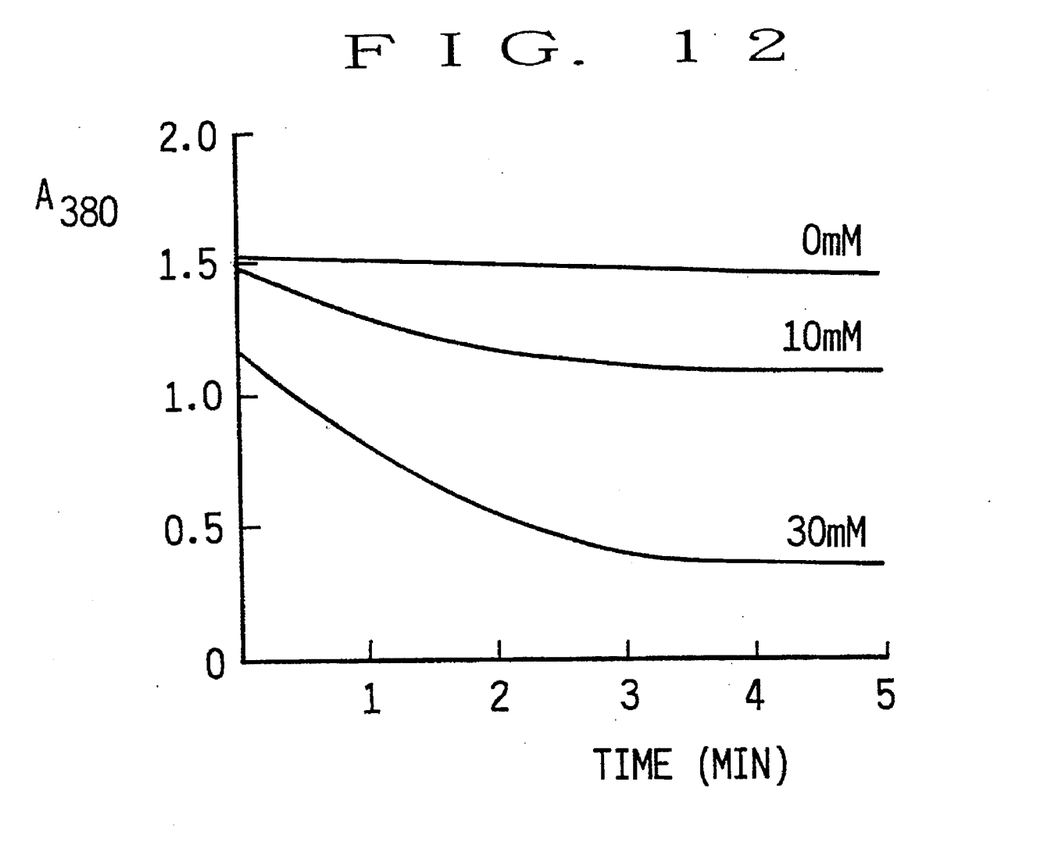
FIG. 12 shows changes in absorbance when the reagent of Example 10 was used.

The above-mentioned reagent (3.0 ml) and a sample (0.1 ml) containing bicarbonate ion (0, 10 or 30 mM) were mixed and allowed to react at 30° C. for 5 minutes. Decrease in absorbance at 380 nm was measured. The results are shown in FIG. 12. When the concentration of magnesium sulfate was 100 mM, the reaction proceeded quickly and ended in 4 minutes.

What is claimed is:

1. A method for measuring carbon dioxide in a liquid sample, comprising the steps of:
   (1) reacting bicarbonate ion in said sample with phosphoenolpyruvate carboxylase and phosphoenolpyruvate;
   (2) reacting the resultant oxalacetic acid with malate dehydrogenase and NADH; and
   (3) measuring the decreased NADH, wherein said phosphoenolpyruvate carboxylase is derived from a species of acetic acid bacteria selected from the group consisting of *Acetobacter pasteurianus*, *Acetobacter xylinum* and *Gluconobacter oxydans*, and said reacting steps (1) and (2) are carried out in a solution containing 50–100 mM magnesium ions and having a pH of 7.5–9.0.

2. The method of claim 1, wherein said phosphoenolpyruvate carboxylase is derived from *Acetobacter pasteurianus*.

3. The method of claim 1, wherein said phosphoenolpyruvate carboxylase is derived from *Acetobacter xylinum*.

4. The method of claim 1, wherein said phosphoenolpyruvate carboxylase is derived from *Gluconobacter oxydans*.

5. The method of claim 1, wherein said solution is a buffer having a pH of 8.0–8.5.

6. The method of claim 1, wherein the step of measuring the decrease in NADH is accomplished by measuring absorbance of a reaction mixture.

7. The method of claim 1, wherein said liquid sample is a body fluid.

8. The method of claim 7, wherein said body fluid is blood serum or blood plasma.

9. A reagent for measuring carbon dioxide, comprising phosphoenolpyruvate, phosphoenolpyruvate carboxylase, malate dehydrogenase, NADH, a butter having a pH of 7.5–9.0 and 50–100 mM magnesium ions, wherein said phosphoenolpyruvate carboxylase is derived from a species of acetic acid bacteria selected from the group consisting of *Acetobacter pasteurianus*, *Acetobacter xylinum* and *Gluconobacter oxydans*.

10. The reagent of claim 9, wherein said phosphoenolpyruvate carboxylase is derived from *Acetobacter pasteurianus*.

11. The reagent of claim 9, wherein said phosphoenolpyruvate carboxylase is derived from *Acetobacter xylinum*.

12. The reagent of claim 9, wherein said phosphoenolpyruvate carboxylase is derived from *Gluconobacter oxydans*.

13. The reagent of claim 9, having a pH of 8.0–8.5.

14. The reagent of claim 9, comprising 10–50 mM weak alkaline buffer, 2–5 mM phosphoenolpyruvate, 50–100 mM magnesium ions, 0.3–1.5 mM NADH, 5–50 U/ml malate dehydrogenase and 0.5–10 U/ml phosphoenolpyruvate carboxylase derived from the acetic acid bacteria.

15. The reagent of claim 9, comprising 10–50 mM weak alkaline buffer, 2–5 mM phosphoenolpyruvate, 50–100 mM magnesium ions, 0.1–0.2 mM NADH, 5–50 U/ml malate dehydrogenase and 0.05–1 U/ml phosphoenolpyruvate carboxylase derived from the acetic acid bacteria.

* * * * *